US00PP37544P2

(12) United States Plant Patent
Avent

(10) Patent No.: US PP37,544 P2
(45) Date of Patent: Jul. 28, 2026

(54) ***YUCCA* PLANT NAMED 'Blue-haired Lady'**

(50) Latin Name: *Yucca rostrata*
Varietal Denomination: Blue-haired Lady

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 0 days.

(21) Appl. No.: 18/831,928

(22) Filed: Nov. 17, 2025

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373, 263.1
CPC ..... A01H 5/12; A01H 5/02
See application file for complete search history.

*Primary Examiner* — Kent L Bell

(57) ABSTRACT

A new and unique *Yucca* plant named 'Blue-haired Lady' is characterized by a trunked-mound of flexible, linear very blue leaves. The plant produces a large foliar mound that is winter hardy. The white flowers are produced on attractive, heavily-branched, upright panicles in the spring. The flowers are hummingbird friendly, and the plant is resistant to deer.

4 Drawing Sheets

Botanical classification: *Yucca rostrata.*
Variety denomination: 'Blue-haired Lady'.

STATEMENT REGARDING PRIOR DISCLOSURES UNDER 37 CFR 1.77(b)(6)

The first offer for sale of *Yucca* 'Blue-haired Lady' sales was by Walters Gardens, Inc. to Plant Delights Nursery, Inc. on Nov. 19, 2024. Walters Gardens, Inc. obtained the new plant and all the information about the new plant from the inventor. No plants have been sold more than one year from the filing date of this application.

BACKGROUND OF THE INVENTION

The present invention relates to the new and distinct *Yucca rostrata* 'Blue-haired Lady', referred to herein by the cultivar name 'Blue-haired Lady' and the new plant. 'Blue-haired Lady' was selected by the inventor in the summer of 1999 at a nursery in Raleigh, North Carolina from open pollinated seedlings from unnamed and unpatented *Yucca rostata* plants obtained from a nursery in Hempstead, Texas. The specific female or seed parent and male or pollen parent are unknown, so no comparison is possible.

The new plant has been successfully asexually propagated by shoot tip tissue culture since 2020 at a wholesale perennial nursery in Zeeland, Michigan. Asexual propagation has been found to produce stable and identical plants that maintain all the unique characteristics of the original plant in successive generations.

BRIEF SUMMARY OF THE INVENTION

'Blue-haired Lady' differs from all other *Yucca rostrata* plants known to the inventor. The nearest comparison cultivars are: 'Sapphire Skies' (not patented) and *Y. rigida* 'Blue Sentry' (not patented).

'Blue-haired Lady' has a noticeably bluer foliage color than 'Sapphire Skies' under greenhouse conditions and even more pronounced bluer color in the full-sun garden. 'Blue Sentry' has stiffer more rigid foliage.

'Blue-haired Lady' is unique from all the above cultivars in possessing the following combined traits:

1. Very blue, linear, flexible foliage;
2. Very large inflorescence which is held above the foliage mound;
3. A robust growth habit.

BRIEF DESCRIPTION OF THE DRAWING

The drawings of *Yucca* 'Blue-haired Lady' demonstrate the overall appearance of the new plant including the unique traits as a twenty-six-year-old plant grown in a full-sun garden in Raleigh, North Carolina. The colors are as accurate as reasonably possible with color reproductions. Ambient light spectrum, temperature, source, and direction may cause the appearance of minor variations in color.

DETAILED BOTANICAL DESCRIPTION

Figure 1:
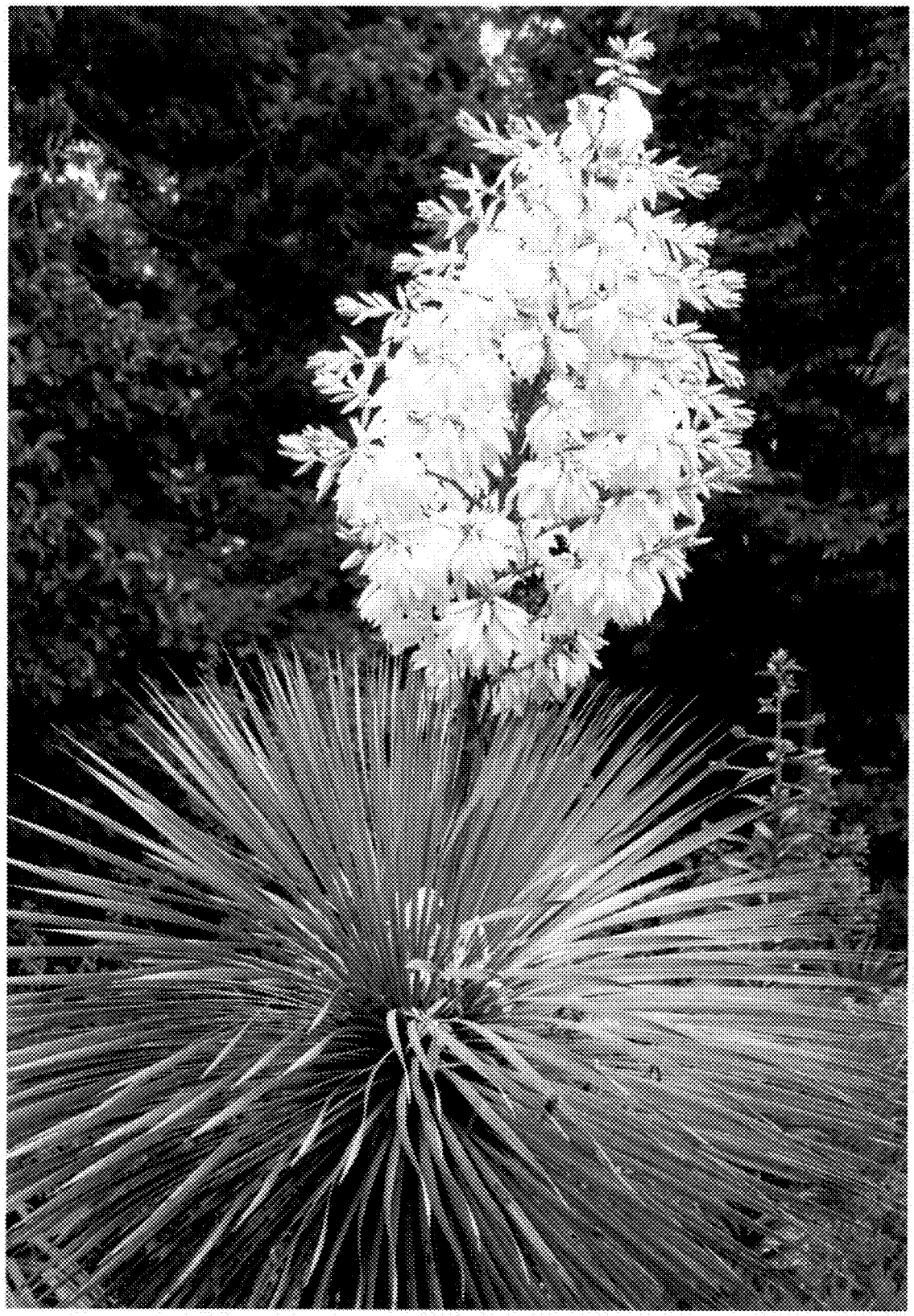
FIG. 1 shows the habit of the new plant in full flower.
Figure 2:
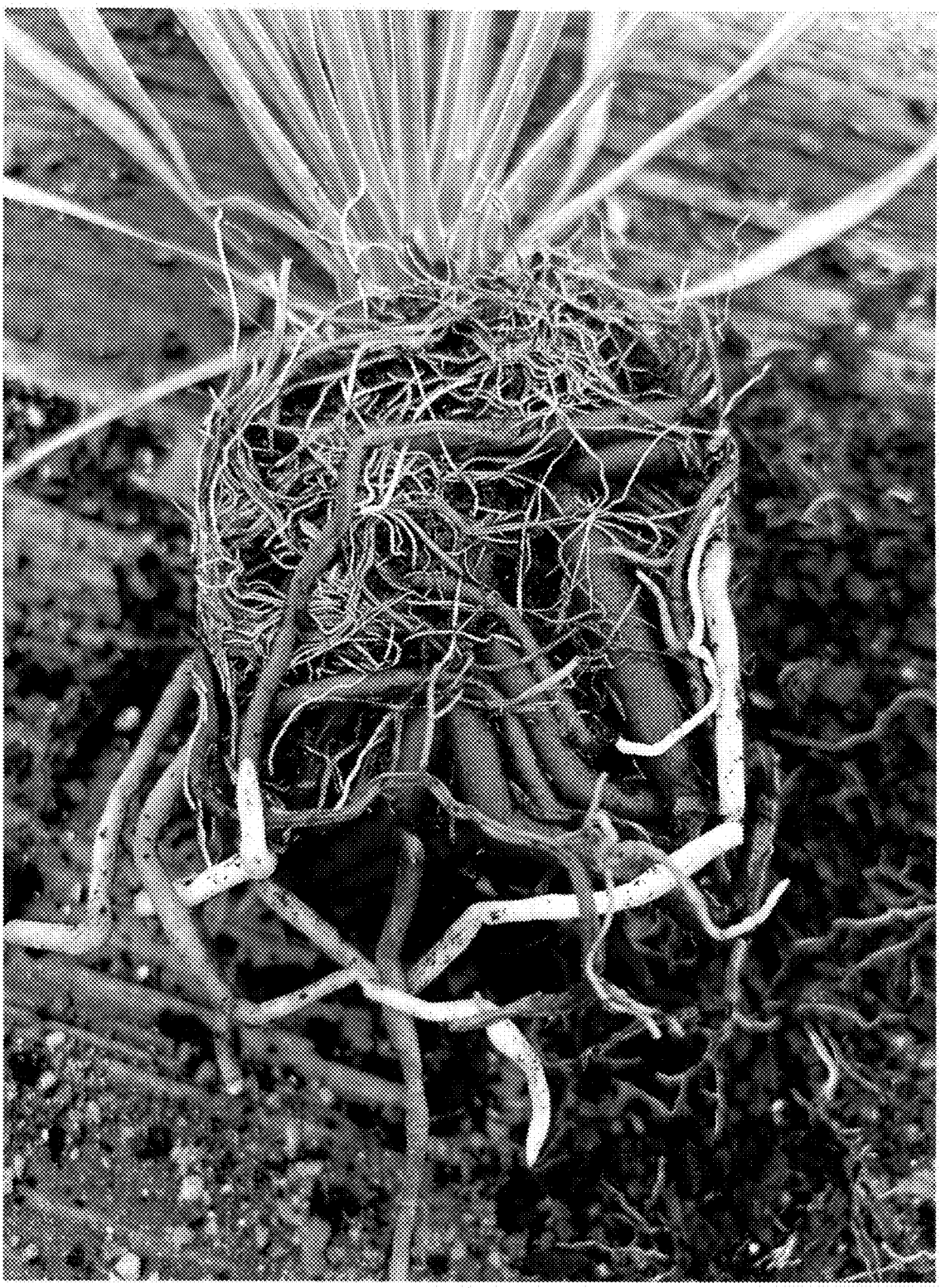
FIG. 2 shows a close-up of plant base and roots from a 0.7-liter pot.
Figure 3:
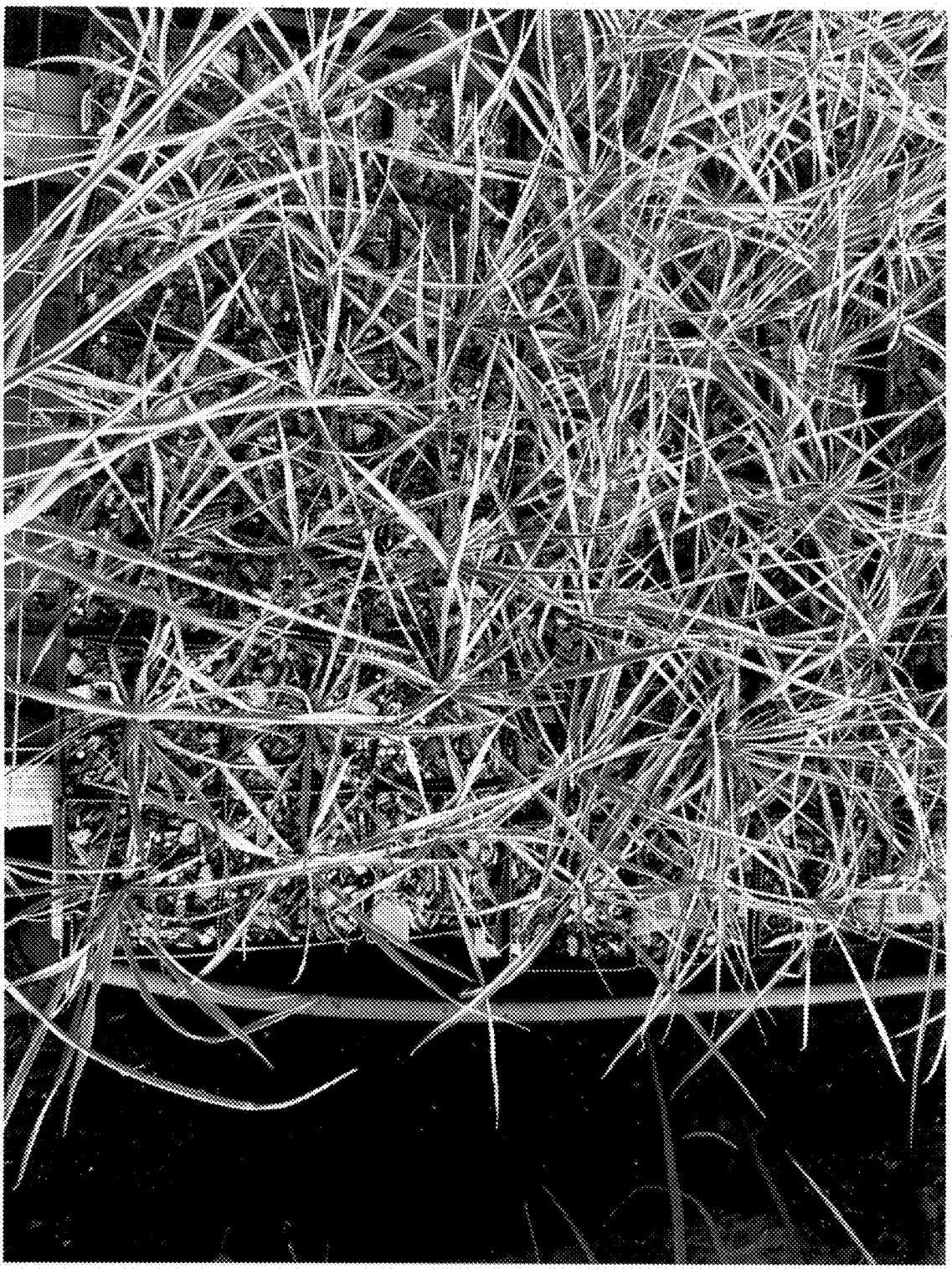
FIG. 3 shows a comparison of 0.7-liter pots of 'Blue-haired Lady' in the three columns of pots on the left and 'Sapphire Skies' in the three columns of pots on the right.
Figure 4:
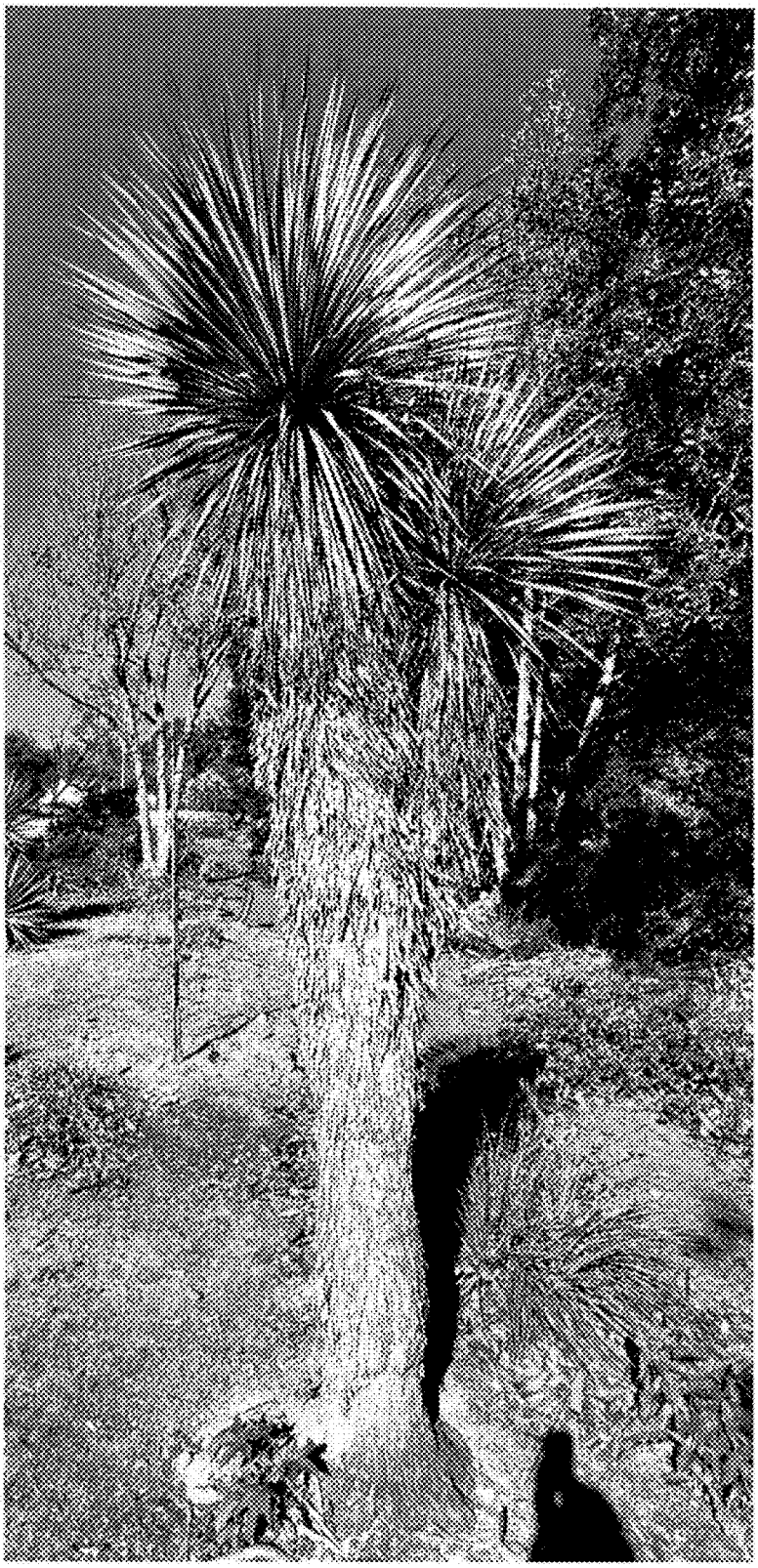
FIG. 4 shows a mature plant in a trial landscape with single occasional branched trunk.

The following descriptions and color references are based on the 1999 edition of The Royal Horticultural Society Colour Chart except where common dictionary terms are used. The new plant, *Yucca* 'Blue-haired Lady', has not been observed under all possible environments. The phenotype may vary slightly with different environmental conditions, such as temperature, light, fertility, moisture, and maturity levels, but without any change in the genotype. The following observations and size descriptions are of a twenty-six-year-old plant in a full-sun garden in Raleigh, North Carolina.

Parentage: The specific female or seed parent and the male or pollen parent are unknown and unnamed selections of *Yucca rostrata;*

Propagation: By sterile shoot-tip tissue culture;

Time to initiate roots from tissue culture: About 21 days;

Growth rate: Moderate;

Crop time: Finishing in a 0.7-liter pot in about one year with plant foliage to about 30.5 cm tall and 30.5 cm wide;

Rooting habit: Fibrous, highly branching; with roots about 25 cm long and 2 mm in diameter in a 0.7-liter pot, increasing with age;

Root color: Variable with age and soil substrate, young roots are white, between RHS 155A and RHS 155B; turning tan, between RHS 172C and RHS 172D; and eventually reddish brown; between RHS 173A and RHS 174A;

Plant shape and habit: Typically, single stemmed, tree-like habit, occasionally developing one or a few assurgent lateral branches with age; with a dense whorl of evergreen leaves radially emerging from a central ligneous stem;

Plant size: To about 206 cm tall to the top of the foliage; and about main head about 127 cm wide;

Stem: To about 25.4 cm diameter; covered with live and dead foliage in the lower portion except about 20 cm of the western side which is furrowed and closest to RHS 202B;

Foliage description: Linear; simple; sessile; bi-laterally symmetrical; coriaceous; apex narrowly acute mucronate; base truncate; margin micro-dentate; spirally arranged; adaxial and abaxial glabrous; not variegated;

Leaf Size: About 58 cm to 67 cm long, about 1.5 cm to 1.7 cm wide near middle, and 2.0 cm to 2.5 cm wide at base;

Foliage fragrance: None observed;

Leaf number: About 120 actively growing per plant;

Leaf blade color:

*Young adaxial.*—Greyed-green closest to RHS 189-B.

*Young abaxial.*—Greyed-green closest to RHS 189-B.

*Mature adaxial.*—Greyed-green closest to RHS 189-B.

*Mature abaxial.*—Greyed-green closest to RHS 189-B.

*Winter adaxial.*—Greyed-green closest to RHS 189-B.

*Winter abaxial.*—Greyed-green closest to RHS 189-B.

*Micro-dentate edge color.*—Closest to RHS 8D; Leaf tip begins senescing about the second year with distal 15 mm to 20 mm color closest to RHS 201B, and by year five the whole leaf is dried with color between RHS 199B and RHS 199C.

Mucro: Sharp; firm; on one-year-old leaves about 3 mm to 4 mm long and color nearly black closest to RHS 202A;

Petiole: Leaves sessile;

Veins: Parallel; glabrous; not obvious; color greyed-green closest to RHS 189-B;

Inflorescence: Highly-branched panicle; extending above and beyond foliage; to about 150 cm tall; flowering portion to about 115 cm tall and about 78 cm across; with about 50 branches per inflorescence;

Peduncle: Cylindrical; glaucous; glabrous; stiff; strong; ligneous; highly-branched; ridged upright; about 150 cm long and 2.7 cm diameter at base; with about 50 compound branches from 21 cm to about 56 cm long and to about 8 mm diameter at base; branches outwardly at about a 110° to 90° angle above horizontal;

Peduncle color: Basal portion before flowering closest to RHS 138A, distal portion and branches closest to RHS 145B;

Pedicel: Not present, flowers sessile;

Inflorescence bracts: About 8 subtending branches; lanceolate; acute apex; partially-clasping truncate base; micro-dentate margin; glabrous;

Inflorescence bract size: Lowest about 31 cm long, 1 cm across, decreasing in size distally to about 13 cm long and 0.6 cm across;

Inflorescence bract color: Initially closest to RHS 189B, drying before anthesis closest to RHS 199D;

Buds one day prior to anthesis: Oblong ellipsoidal; acute apex; truncate base; about 5.5 cm long and about 1.5 cm across at widest portion near middle;

Bud color: Closest to RHS 155D with a faint undertone closest to RHS 157C;

Flower description: Campanulate; zygomorphic; perfect; incomplete; to about 6.5 cm long and opening to about 6 cm across; flowers individually lasting about one week; flowering period about three weeks in spring;

Flower fragrance: Slight;

Tepals: Six arranged in a whorl; narrowly to broadly ovate; slightly concavo-convex; acuminate apex; rounded base; margin entire; glaucous and glabrous abaxial and adaxial; about 6.5 cm long; outer set about 1.3 cm wide; inner set about 2.2 cm wide;

Tepal color: Initial adaxial and abaxial closest to RHS 155D; mature adaxial and abaxial lighter and more white than RHS 155D;

Androecium: Six;

*Filaments.*—Six; cylindrical; straight; about 3.2 cm long, 2 mm across; color lighter and more white than RHS 155D.

*Anther.*—Six; cylindrical; about 0.6 cm long and about 0.4 mm diameter; color lighter and more white than RHS 155D.

*Pollen.*—Abundant; color whiter than RHS 155D.

Gynoecium: Single; three-chambered; superior;

*Style.*—Cylindrical; about 1 cm long and 3 mm wide at base; color lighter and more white than RHS 155D.

*Stigma.*—Three-lobed; upright; about 0.75 cm wide; color lighter and more white than RHS 155D.

*Ovary.*—Superior; cylindrical; about 12 mm long and 5 mm across at base; color between RHS 146D and RHS 145D.

Fruit: Tri-locule dehiscent capsule; cylindrical with terminal rostrum; about 5 cm to 8 cm long and 1 cm to 2 cm diameter; color initially closest to RHS 199D maturing to variable colors closest to RHS 200C and RHS 202A;

Seed: Dry; papery; glabrous; roughly semi-circular; thin; color closest to RHS 202A;

Disease resistance and pest: *Yucca* 'Blue-haired Lady' has no major pests but has not been observed to be resistant or susceptible to diseases and pests beyond that which is normal for other *Yucca.*

Growth and hardiness: The new plant tolerates part sun but performs best in full sun. It is xeromorphic and survives well with minimal water once established. The new plant is hardy to winter temperatures of −15° C. and summer highs of over 37° C. Full extent of winter hardiness has not been tested.

It is claimed:

1. A new and distinct cultivar of ornamental *Yucca* plant named 'Blue-haired Lady' as herein described and illustrated.

* * * * *